US008785165B2

(12) United States Patent
Lee et al.

(10) Patent No.: US 8,785,165 B2
(45) Date of Patent: *Jul. 22, 2014

(54) SINGLE PH PROCESS FOR STARCH LIQUEFACTION AND SACCHARIFICATION FOR HIGH-DENSITY GLUCOSE SYRUPS

(75) Inventors: Sung Ho Lee, North Liberty, IA (US); Jayarama K. Shetty, Pleasanton, CA (US); Paula Johanna Maria Teunissen, Voorschoten (NL)

(73) Assignee: Danisco US Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/113,557

(22) PCT Filed: Apr. 27, 2012

(86) PCT No.: PCT/US2012/035413
§ 371 (c)(1),
(2), (4) Date: Dec. 11, 2013

(87) PCT Pub. No.: WO2012/149288
PCT Pub. Date: Nov. 1, 2012

(65) Prior Publication Data
US 2014/0087430 A1    Mar. 27, 2014

Related U.S. Application Data

(60) Provisional application No. 61/481,084, filed on Apr. 29, 2011.

(51) Int. Cl.
*C12P 7/36* (2006.01)
*C12P 7/10* (2006.01)
*C12N 9/34* (2006.01)

(52) U.S. Cl.
USPC .......................... 435/151; 435/165; 435/205

(58) Field of Classification Search
USPC ......................................... 435/165, 151, 205
See application file for complete search history.

(56) References Cited

U.S. PATENT DOCUMENTS

| | | |
|---|---|---|
| 4,247,637 A | 1/1981 | Tamura et al. |
| 4,618,579 A | 10/1986 | Dwiggins et al. |
| 4,794,175 A | 12/1988 | Nunberg et al. |
| 4,863,864 A | 9/1989 | Ashikari et al. |
| 5,024,941 A | 6/1991 | Maine et al. |
| 5,246,853 A | 9/1993 | Clarkson et al. |
| 5,254,467 A | 10/1993 | Kretschmann et al. |
| 5,464,760 A | 11/1995 | Tsai et al. |
| 5,475,101 A | 12/1995 | Ward et al. |
| 5,847,276 A | 12/1998 | Mimken et al. |
| 6,022,725 A | 2/2000 | Fowler et al. |
| 6,255,084 B1 | 7/2001 | Nielsen et al. |
| 6,265,190 B1 | 7/2001 | Yedur et al. |
| 6,268,328 B1 | 7/2001 | Mitchinson et al. |
| RE37,393 E | 9/2001 | Donnelly et al. |
| 6,303,352 B1 | 10/2001 | Cameron et al. |
| 6,440,716 B1 | 8/2002 | Svendsen et al. |
| 6,596,521 B1 | 7/2003 | Chang et al. |
| 6,620,924 B2 | 9/2003 | Nielsen et al. |
| 7,262,041 B2 | 8/2007 | Baldwin et al. |
| 7,320,882 B2 | 1/2008 | Rieping |
| 7,332,309 B2 | 2/2008 | Rieping |
| 7,666,634 B2 | 2/2010 | Rieping et al. |
| 2006/0281157 A1 | 12/2006 | Chotani et al. |
| 2009/0305360 A1 | 12/2009 | Breneman et al. |
| 2009/0305935 A1 | 12/2009 | Cascao-Pereira et al. |
| 2010/0015686 A1 | 1/2010 | Cascao-Pereira et al. |

FOREIGN PATENT DOCUMENTS

| | | |
|---|---|---|
| EP | 0215594 | 3/1987 |
| EP | 0244234 | 11/1987 |
| WO | WO8809795 | 12/1988 |
| WO | WO9206209 | 4/1992 |
| WO | WO9526397 | 10/1995 |
| WO | WO03066816 | 8/2003 |
| WO | WO03095659 | 11/2003 |
| WO | WO2005001036 | 1/2005 |
| WO | WO2005052148 | 6/2005 |
| WO | WO2005082155 | 9/2005 |
| WO | WO2008086811 | 7/2008 |
| WO | WO2009048487 | 4/2009 |
| WO | WO2009048488 | 4/2009 |
| WO | WO2009067218 | 5/2009 |
| WO | WO2009099783 | 8/2009 |
| WO | WO2009149283 | 12/2009 |

OTHER PUBLICATIONS

Accession No. D86235, Takashima, et al., "*Trichoderma reesei* cbhl gene for cellobiohydrolase I, upstream region", GenBank: D86235.1, (1997), http://www.ncbi.nlm.nih.gov/nucleotide/D86235.

Aleshin, et al., "Refined crystal structures of glucoamylase from *Aspergillus awamori* var. x100", J Mol Biol, (1994), 238:575-91.

Ashikari, et al., "Direct fermentation of raw corn to ethanol by yeast transformants containing a modified *Rhizopus* glucoamylase gene", Appl Microbiol Biotechnol, (1989), 32:129-33.

Ashikari, et al., "*Rhizopus* raw-starch-degrading glucoamylase: its cloning and expression in yeast", Agric Biol Chem, (1986), 50:957-64.

Bennet, et al., "More gene manipulations in fungi", Academic Press, (1991), 70-6.

Bhikhabhai, et al., "Isolation of cellulolytic enzymes from *Trichoderma reesei* QM 9414", J Appl Biochem, (1984), 6:336-45.

Boel, et al., "Glucoamylases G1 and G2 from *Aspergillus niger* are synthesized from two different but closely related mRNA", EMBO J, (1984), 3:1097-102 (1984).

Boel, et al., "Two different types of intervening sequences in the glucoamylase gene from *Aspergillus niger*", EMBO J, (1984), 3:1581-5.

(Continued)

*Primary Examiner* — Maryam Monshipouri
(74) *Attorney, Agent, or Firm* — Danisco US Inc.

(57) ABSTRACT

Embodiments of the present disclosure relate to a process for producing downstream products, such as high-density glucose syrups and high-glucose fermentation feedstock, from a starch-containing substrate without a pH adjustment before the saccharification step. The saccharification is effectively catalyzed by a glucoamylase at a pH in the range of 5.2 to 5.6.

19 Claims, 3 Drawing Sheets

(56) References Cited

OTHER PUBLICATIONS

Brumbauer, et al., "Fractionation of cellulase and beta-glucosidase in a *Trichoderma reesei* culture liquid by use of two-phase partitioning", Bioseparation, (1999), 7:287-95.

Campbell, et al., "Improved transformation efficiency of *Aspergillus niger* using the homologous niaD gene for nitrate reductase", Curr Genet, (1989), 16:53-6.

Ellouz, et al., "Analytical separation of *Trichoderma reesei* cellulases by ion-exchange fast protein liquid chromatography", J Chroma, 396, (1987), 307-317.

Finkelstein, et al., "Transformation", Biotechnology, (1992), 21:113-56.

Fliess, et al., "Characterization of cellulases by HPLC separation", Eur J Appl Microbiol Biotechnol, (1983), 17:314-18.

Goedegebuur, et al., "Cloning and relational analysis of 15 novel fungal endoglucanases from family 12 glycosyl hydrolase", Curr Genet, (2002), 41:89-98.

Goyal, et al., "Characteristics of fungal cellulases", Biores Technol, (1991), 36:37-50.

Harkki, et al., "A novel fungal expression system: secretion of active calf chymosin from the filamentous fungus *Trichoderma reesei*", Bio Technol, (1989), 7:596-603.

Harkki, et al., "Genetic engineering of *Trichoderma* to produce strains with novel cellulase profiles", Enzyme Microb Technol, (1991), 13:227-33.

Hayashida, et al., "Molecular cloning of the glucoamylase I gene of *Aspergillus awamori* var. kawachi for localization of the raw-starch-affinity site", Agric Biol Chem, (1989), 53:923-9.

Houghton-Larsen, et al., "Cloning and characterisation of a glucoamylase gene (GlaM) from the dimorphic zygomycete *Mucor circinelloides*", Appl Microbiol Biotechnol, (2003), 62:210-7.

Ilmen, et al., "Regulation of cellulase gene expression in the filamentous fungus *Trichoderma reesei*", Appl Environ Microbiol, (1997), 63:1298-306.

Innis, et al., "Expression, Glycosylation, and Secretion of an *Aspergillus* Glucoamylase by *Saccharomyces cerevisiae*", Science, (1985), 228:21-6.

Kelly, et al., "Transformation of *Aspergillus niger* by the amdS gene of *Aspergillus nidulans*", EMBO J, (1985), 4:475-9.

Linko, et al., "Simultaneous liquefaction, saccharification, and lactic acid fermentation on barley starch", Enz Microb Technol, (1996), 19:118-23.

Medve, et al., "Ion-exchange chromatographic purification and quantitative analysis of *Trichoderma reesei* cellulases cellobiohydrolase I, II and endoglucanase II by fast protein liquid chromatography", J Chroma, (1998), 808:153-165.

Mercier, et al., "Kinetics of lactic acid fermentation on glucose and corn by *Lactobacillus amylophilus*", J Chem Tech Biotechnol, (1992), 55:111-21.

Nevalainen, et al., "The Molecular Biology of *Trichoderma* and its Application to the Expression of Both Homologous and Heterologous Genes", Molecular Biology of *Trichoderma*, (1992), 129-48.

Nunberg, et al., "Molecular cloning and characterization of the glucoamylase gene of *Aspergillus awamori*", Mol Cell Biol, (1984), 4:2306-15.

Penttila, et al., "A versatile transformation system for the cellulolytic filamentous fungus *Trichoderma reesei*", Gene, (1987), 61:155-64.

Pourquie, et al., "Scale up of cellulase production and utilization", Biochemistry and Genetics of Cellulose Degradation, eds. Aubert, J. P. et al., Academic Press, (1988), 71-86.

Sheir-Neiss, et al., "Characterization of the secreted cellulases of *Trichoderma reesei* wild type and mutants during controlled feremntations", Appl Microbiol Biotechnol, (1984), 20:46-53.

Svensson, et al., "The complete amino acid sequence of the glycoprotein, glucoamylase G1, from *Aspergillus niger*", Carlsberg Res Commun, (1983), 48:529-44.

Tilbeurgh, et al., "Separation of endo- and exo-type cellulases using a new affinity chromatography method", FEBS Lett., (1984), 16:215-18.

Tomaz, et al., "Studies on the chromatographic fractionation of *Trichoderma reesei* cellulases by hydrophobic interaction", J Chromatogr A, (1999), 865:123-8.

Tsai, et al., "An integrated bioconversion process for production of L-lactic acid from starchy potato feedstocks", Appl Biochem Biotechnol, (1998), 70-72:417-28.

van den Hondel, et al., "Heterologous gene expression in filamentous fungi", (1991), in Bennett and Lasure (Eds.) More Gene Manipulations in Fungi, Academic Press, 396-428.

Ward, et al., "Use of *Aspergillus* overproducing mutants, cured for integrated plasmid, to overproduce heterologous proteins", Appl. Microbiol. Biotechnol., (1993), 39:738-43.

Zhang, et al., "Direct fermentation of starch to lactic acid by *Lactobacillus amylovorus*", (1991), Biotechnol. Lett., 13:733-8.

Zhang, et al., "Production of L-alanine by metabolically engineered *Escherichia coli*", Appl. Microbiol. Biotechnol., (2007), 77:355-66.

SEQUENCE LISTING

```
<160> NUMBER OF SEQ ID NOS: 3

<210> SEQ ID NO 1
<211> LENGTH: 2103
<212> TYPE: DNA
<213> ORGANISM: Humicola grisea

<400> SEQUENCE: 1
atgcatacct tctccaagct cctcgtcctg ggctctgccg tccagtctgc cctcgggcgg      60
cctcacggct cttcgcgtct ccaggaacgc gctgccgttg ataccttcat caacaccgag     120
aagcccatcg catggaacaa gctgctcgcc aacatcggcc ctaacggcaa agccgctccc     180
ggtgccgccg ccggcgttgt gattgccagc ccttccagga cggaccctcc ttgtacgtgg     240
tggcatggaa tggacccaag agactggttt tagatgaaag agagtttctg ctaaccgcca     300
cacccagact tcttcacctg gacccgcgat gccgccctgg tcctcaccgg catcatcgag     360
tcccttggcc acaactacaa caccaccctg cagaccgtca tccagaacta cgtcgcgtcg     420
caggccaagc tgcagcaggt ctcgaacccc tcgggaacct tcgccgacgg ctcgggtctc     480
ggtgaggcca agttcaatgt cgacctcact gccttcactg gcgaatgggg tcgccctcag     540
agggacggcc cgcccctgcg cgccatcgct ctcatccagt acgccaagtg gctgatcgcc     600
aacggctaca gagcacggc caagagcgtc gtctggcccg tcgtcaagaa cgatctcgcc     660
tacacggccc agtactggaa cgagaccggc ttcgatctct gggaggaggt ccccggcagc     720
tcgttcttta ccatcgccag ctctcacagg ggtgagtcat ttattgttca gtgttttctc     780
attgaataat taccggaatg ccactgacgc caaacagctc tgactgaggg tgcttacctc     840
gccgctcagc tcgacaccga gtgccgcgcc tgcacgaccg tcgccctca ggttctgtgc      900 ttccagcagg ccttctggaa ctccaagggc aactatgtcg tctccaacag taagatccct     960
acaccaacaa aaaaaatcga aaaggaacgt tagctgaccc ttctagtcaa cggcggcgag    1020 tatgctccg gcaaggacgc caactcgatc ctggcgtcca tccacaactt cgaccctgag    1080
gccggctgcg acaacctgac cttccagccc tgcagcgagc gcgccctggc caaccacaag    1140
```

```
gcctatgtcg actcgttccg caacctctac gccatcaaca agggcatcgc ccagggcaag   1200
gccgttgccg tcggccgcta ctcggaggat gtctactaca acggcaaccc gtggtacctg   1260
gccaactttg ccgccgccga gcagctctac gacgccatct acgtgtggaa caagcagggc   1320
tccatcaccg tgacctcggt ctccctgccc ttcttccgcg accttgtctc gtcggtcagc   1380
accggcacct actccaagag cagctcgacc ttcaccaaca tcgtcaacgc cgtcaaggcc   1440
tacgccgacg gcttcatcga ggtggcggcc aagtacaccc cgtccaacgg cgcgctcgcc   1500
gagcagtacg accgcaacac gggcaagccc gactcggccg ccgacctgac gtggtcgtac   1560
tcggccttcc tctcggccat cgaccgccgc gcgggtctcg tcccccgag ctggcgggcc   1620 agcgtggcca agagccagct gccgtccacc tgctcgcgca tcgaggtcgc cggcacctac   1680
gtcgccgcca cgagcacctc gttcccgtcc aagcagaccc cgaaccccte cgcggcgccc   1740 tccccgtccc cctacccgac cgcctgcgcg gacgctagcg aggtgtacgt caccttcaac   1800
gagcgcgtgt cgaccgcgtg gggcgagacc atcaaggtgg tgggcaacgt gccggcgctg   1860
gggaactggg acacgtccaa ggcggtgacc ctgtcggcca gcgggtacaa gtcgaatgat   1920
cccctctgga gcatcaccgg tgcccatcaag gcgacgggct cggccgtgca gtacaagtat   1980
atcaaggtcg gcaccaacgg gaagattact tgggagtcgg accccaacag gagcattacc   2040
ctgcagacgg cgtcgtctgc gggcaagtgc gccgcgcaga cggtgaatga ttcgtggcgt   2100
taa                                                                2103

<210> SEQ ID NO 2
<211> LENGTH: 634
<212> TYPE: PRT
<213> ORGANISM: Humicola grisea

<400> SEQUENCE: 2

Met His Thr Phe Ser Lys Leu Leu Val Leu Gly Ser Ala Val Gln Ser
1               5                   10                  15

Ala Leu Gly Arg Pro His Gly Ser Ser Arg Leu Gln Glu Arg Ala Ala
                20                  25                  30

Val Asp Thr Phe Ile Asn Thr Glu Lys Pro Ile Ala Trp Asn Lys Leu
            35                  40                  45

Leu Ala Asn Ile Gly Pro Asn Gly Lys Ala Ala Pro Gly Ala Ala
        50                  55                  60

Gly Val Val Ile Ala Ser Pro Ser Arg Thr Asp Pro Pro Tyr Phe Phe
65                  70                  75                  80

Thr Trp Thr Arg Asp Ala Ala Leu Val Leu Thr Gly Ile Ile Glu Ser
                85                  90                  95

Leu Gly His Asn Tyr Asn Thr Thr Leu Gln Thr Val Ile Gln Asn Tyr
            100                 105                 110

Val Ala Ser Gln Ala Lys Leu Gln Gln Val Ser Asn Pro Ser Gly Thr
        115                 120                 125

Phe Ala Asp Gly Ser Gly Leu Gly Glu Ala Lys Phe Asn Val Asp Leu
    130                 135                 140

Thr Ala Phe Thr Gly Glu Trp Gly Arg Pro Gln Arg Asp Gly Pro Pro
145                 150                 155                 160

Leu Arg Ala Ile Ala Leu Ile Gln Tyr Ala Lys Trp Leu Ile Ala Asn
                165                 170                 175

Gly Tyr Lys Ser Thr Ala Lys Ser Val Val Trp Pro Val Val Lys Asn
            180                 185                 190
```

-continued

```
Asp Leu Ala Tyr Thr Ala Gln Tyr Trp Asn Glu Thr Gly Phe Asp Leu
            195                 200                 205

Trp Glu Glu Val Pro Gly Ser Ser Phe Phe Thr Ile Ala Ser Ser His
210                 215                 220

Arg Ala Leu Thr Glu Gly Ala Tyr Leu Ala Ala Gln Leu Asp Thr Glu
225                 230                 235                 240

Cys Arg Ala Cys Thr Thr Val Ala Pro Gln Val Leu Cys Phe Gln Gln
                245                 250                 255

Ala Phe Trp Asn Ser Lys Gly Asn Tyr Val Val Ser Asn Ile Asn Gly
                260                 265                 270

Gly Glu Tyr Arg Ser Gly Lys Asp Ala Asn Ser Ile Leu Ala Ser Ile
                275                 280                 285

His Asn Phe Asp Pro Glu Ala Gly Cys Asp Asn Leu Thr Phe Gln Pro
                290                 295                 300

Cys Ser Glu Arg Ala Leu Ala Asn His Lys Ala Tyr Val Asp Ser Phe
305                 310                 315                 320

Arg Asn Leu Tyr Ala Ile Asn Lys Gly Ile Ala Gln Gly Lys Ala Val
                325                 330                 335

Ala Val Gly Arg Tyr Ser Glu Asp Val Tyr Tyr Asn Gly Asn Pro Trp
                340                 345                 350

Tyr Leu Ala Asn Phe Ala Ala Ala Glu Gln Leu Tyr Asp Ala Ile Tyr
                355                 360                 365

Val Trp Asn Lys Gln Gly Ser Ile Thr Val Thr Ser Val Ser Leu Pro
                370                 375                 380

Phe Phe Arg Asp Leu Val Ser Ser Val Ser Thr Gly Thr Tyr Ser Lys
385                 390                 395                 400

Ser Ser Ser Thr Phe Thr Asn Ile Val Asn Ala Val Lys Ala Tyr Ala
                405                 410                 415

Asp Gly Phe Ile Glu Val Ala Ala Lys Tyr Thr Pro Ser Asn Gly Ala
                420                 425                 430

Leu Ala Glu Gln Tyr Asp Arg Asn Thr Gly Lys Pro Asp Ser Ala Ala
                435                 440                 445

Asp Leu Thr Trp Ser Tyr Ser Ala Phe Leu Ser Ala Ile Asp Arg Arg
                450                 455                 460

Ala Gly Leu Val Pro Pro Ser Trp Arg Ala Ser Val Ala Lys Ser Gln
465                 470                 475                 480

Leu Pro Ser Thr Cys Ser Arg Ile Glu Val Ala Gly Thr Tyr Val Ala
                485                 490                 495

Ala Thr Ser Thr Ser Phe Pro Ser Lys Gln Thr Pro Asn Pro Ser Ala
                500                 505                 510

Ala Pro Ser Pro Ser Pro Tyr Pro Thr Ala Cys Ala Asp Ala Ser Glu
                515                 520                 525

Val Tyr Val Thr Phe Asn Glu Arg Val Ser Thr Ala Trp Gly Glu Thr
530                 535                 540

Ile Lys Val Val Gly Asn Val Pro Ala Leu Gly Asn Trp Asp Thr Ser
545                 550                 555                 560

Lys Ala Val Thr Leu Ser Ala Ser Gly Tyr Lys Ser Asn Asp Pro Leu
                565                 570                 575

Trp Ser Ile Thr Val Pro Ile Lys Ala Thr Gly Ser Ala Val Gln Tyr
                580                 585                 590

Lys Tyr Ile Lys Val Gly Thr Asn Gly Lys Ile Thr Trp Glu Ser Asp
                595                 600                 605

Pro Asn Arg Ser Ile Thr Leu Gln Thr Ala Ser Ser Ala Gly Lys Cys
```

```
                    610                 615                 620
Ala Ala Gln Thr Val Asn Asp Ser Trp Arg
625                 630

<210> SEQ ID NO 3
<211> LENGTH: 604
<212> TYPE: PRT
<213> ORGANISM: Humicola grisea

<400> SEQUENCE: 3

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65                  70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110

Asp Leu Thr Ala Phe Thr Gly Glu Trp Gly Arg Pro Gln Arg Asp Gly
        115                 120                 125

Pro Pro Leu Arg Ala Ile Ala Leu Ile Gln Tyr Ala Lys Trp Leu Ile
130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205

Thr Glu Cys Arg Ala Cys Thr Thr Val Ala Pro Gln Val Leu Cys Phe
210                 215                 220

Gln Gln Ala Phe Trp Asn Ser Lys Gly Asn Tyr Val Val Ser Asn Ile
225                 230                 235                 240

Asn Gly Gly Glu Tyr Arg Ser Gly Lys Asp Ala Asn Ser Ile Leu Ala
                245                 250                 255

Ser Ile His Asn Phe Asp Pro Glu Ala Gly Cys Asp Asn Leu Thr Phe
            260                 265                 270

Gln Pro Cys Ser Glu Arg Ala Leu Ala Asn His Lys Ala Tyr Val Asp
        275                 280                 285

Ser Phe Arg Asn Leu Tyr Ala Ile Asn Lys Gly Ile Ala Gln Gly Lys
290                 295                 300

Ala Val Ala Val Gly Arg Tyr Ser Glu Asp Val Tyr Tyr Asn Gly Asn
305                 310                 315                 320

Pro Trp Tyr Leu Ala Asn Phe Ala Ala Glu Gln Leu Tyr Asp Ala
                325                 330                 335

Ile Tyr Val Trp Asn Lys Gln Gly Ser Ile Thr Val Thr Ser Val Ser
            340                 345                 350
```

```
Leu Pro Phe Phe Arg Asp Leu Val Ser Ser Val Ser Thr Gly Thr Tyr
        355                 360                 365

Ser Lys Ser Ser Ser Thr Phe Thr Asn Ile Val Asn Ala Val Lys Ala
    370                 375                 380

Tyr Ala Asp Gly Phe Ile Glu Val Ala Ala Lys Tyr Thr Pro Ser Asn
385                 390                 395                 400

Gly Ala Leu Ala Glu Gln Tyr Asp Arg Asn Thr Gly Lys Pro Asp Ser
                405                 410                 415

Ala Ala Asp Leu Thr Trp Ser Tyr Ser Ala Phe Leu Ser Ala Ile Asp
                420                 425                 430

Arg Arg Ala Gly Leu Val Pro Pro Ser Trp Arg Ala Ser Val Ala Lys
            435                 440                 445

Ser Gln Leu Pro Ser Thr Cys Ser Arg Ile Glu Val Ala Gly Thr Tyr
    450                 455                 460

Val Ala Ala Thr Ser Thr Ser Phe Pro Ser Lys Gln Thr Pro Asn Pro
465                 470                 475                 480

Ser Ala Ala Pro Ser Pro Ser Pro Tyr Pro Thr Ala Cys Ala Asp Ala
                485                 490                 495

Ser Glu Val Tyr Val Thr Phe Asn Glu Arg Val Ser Thr Ala Trp Gly
                500                 505                 510

Glu Thr Ile Lys Val Val Gly Asn Val Pro Ala Leu Gly Asn Trp Asp
        515                 520                 525

Thr Ser Lys Ala Val Thr Leu Ser Ala Ser Gly Tyr Lys Ser Asn Asp
    530                 535                 540

Pro Leu Trp Ser Ile Thr Val Pro Ile Lys Ala Thr Gly Ser Ala Val
545                 550                 555                 560

Gln Tyr Lys Tyr Ile Lys Val Gly Thr Asn Gly Lys Ile Thr Trp Glu
                565                 570                 575

Ser Asp Pro Asn Arg Ser Ile Thr Leu Gln Thr Ala Ser Ser Ala Gly
                580                 585                 590

Lys Cys Ala Ala Gln Thr Val Asn Asp Ser Trp Arg
        595                 600
```

SINGLE PH PROCESS FOR STARCH LIQUEFACTION AND SACCHARIFICATION FOR HIGH-DENSITY GLUCOSE SYRUPS

CROSS REFERENCE TO RELATED APPLICATIONS

The present application is a 371 National Stage application of PCT/US2012/035413, filed on Apr. 27, 2012, which claims priority to U.S. Provisional Application Ser. No. 61/481,084, filed on Apr. 29, 2011, which is hereby incorporated by reference in its entirety.

SEQUENCE LISTING

The sequence listing submitted via EFS, in compliance with 37 C.F.R. §1.52(e), is incorporated herein by reference. The sequence listing text file submitted via EFS contains the file "31411WO-2 ST25.txt" created on Sep. 24, 2013, which is 16,384 bytes in size.

FIELD OF THE INVENTION

A process for producing downstream products, such as high-density glucose syrup and fermentation feedstock, from starch-containing material (e.g., grain) without a pH adjustment between liquefaction and saccharification.

BACKGROUND OF THE INVENTION

Typically, glucose can be the product of starch processing, which may be a two-step enzymatic process that catalyzes the breakdown of starch, involving liquefaction and saccharification. During liquefaction, insoluble granular starch is usually slurried in water, gelatinized with heat, and hydrolyzed by a thermostable alpha-amylase. The alpha amylases currently used in most commercial liquefaction processes are not stable at acidic levels of pH 4.8 to pH 5.2, and therefore the pH of the slurry is adjusted to about pH 5.6 to 6.0 using suitable alkali (e.g., sodium or calcium hydroxide, sodium carbonate or ammonia). Therefore, liquefaction is normally carried out at pH of about 5.6 to 6.0.

During saccharification, the soluble dextrins produced in liquefaction are further hydrolyzed by glucoamylases to produce sugars. Glucoamylases are exo-acting carbohydrases, capable of hydrolyzing both the linear and branched glucosidic linkages of starch (e.g., amylose and amylopectin). Commercially available glucoamylases typically have pH optimum in the acidic pH ranges (less than 5.0). As a result, pH of the liquefact is typically adjusted to acidic, in the range of about 4.2-4.5, using for example a diluted acid (e.g., sulfuric acid), to carry out saccharification. Therefore, currently liquefaction and saccharification processes for obtaining a desired end product, such as high density glucose syrups and high-glucose fermentation feedstock, are carried out at different pH levels. The fermentable sugars, e.g., low molecular sugars, such as glucose, may then be converted to fructose by other enzymes (e.g., glucose isomerases); crystallized; or used in fermentations to produce numerous end products (e.g., alcohols, monosodium glutamate, succinic acid, vitamins, amino acids, 1,3-propanediol, and lactic acid).

Because of the necessity to adjust pH levels after liquefaction and before saccharification, the currently available methods of processing starch-containing material require the use of extra chemicals, which increases production costs. The pH adjustments required after the liquefaction step to provide appropriate conditions for saccharification may also result in high salt accumulation in the reaction medium and a high sulphur content, creating an environmental disposal problem. Therefore, a need exists for a method of producing end products, such as high-density glucose syrups and high-glucose fermentation feedstock, commercially without having to carry out liquefaction and saccharification at different pH levels.

SUMMARY OF THE INVENTION

A method is provided for producing high-density glucose syrups and high-glucose fermentation feedstock by a single-pH process, without having to adjust the pH after liquefaction and before saccharification. The method takes advantage of the distinguishing properties of certain glucoamylases. Glucoamylases such as *Humicola grisea* glucoamylase (HgGA) and its variants have a higher pH optimum than known glucoamylases (GAs), such as, for example, GAs from *Aspergillus niger* (AnGA) and *Talaromyces emersonii* (TeGA). Therefore, the glucoamylases used in the present method are capable of saccharifying a starch substrate to produce high density glucose syrups and high-glucose fermentation feedstock effectively at a pH in the range of 5.2-5.6 and at a temperature in the range of about 58° C. to about 62° C. This property of the HgGA glucoamylases enables them to be used in a single-pH process for starch liquefaction and saccharification to produce high density glucose syrups and high-glucose fermentation feedstock. The presently disclosed methods can also combine the glucoamylases with a pullulanase to increase the process efficiency.

In one aspect, the glucoamylase is selected from the group consisting of a parent *Humicola grisea* glucoamylase (HgGA) comprising SEQ ID NO: 3 and a variant thereof, wherein the variant has at least 99% identity to the parent glucoamylase. In another aspect, the glucoamylase has one amino acid modification compared to the parent glucoamylase. In a further aspect, the glucoamylase is HgGA having amino acid sequence of SEQ ID NO: 3. Optionally, the glucoamylase is produced in a *Trichoderma reesei* host cell.

In one embodiment, the glucoamylase is added at a dose of at least about 0.15 GAU per gram of dry substance starch, or at least about 0.20 GAU per gram of dry substance starch.

In one aspect, the saccharification is carried out at pH 5.35 to 5.5. In another aspect, the starch substrate used for the saccharification is liquefied starch. In a further aspect, the saccharification achieves a DP1 concentration of at least 95% at about 70 hours.

In one embodiment, the starch substrate is about 30% to about 50%, or about 30% to about 35% dry solids (DS).

In another aspect the starch substrate is granular starch and saccharification achieves a DP1 concentration of at least 95% at about 28 hours and the starch solubility of the starch substrate is at least 90%.

In one embodiment saccharification achieves a DP1 concentration of at least 96% at about 50 hours and the starch solubility of the starch substrate is at least 97%.
Additionally, the higher sugar content can be below 1%. Furthermore, the starch substrate can be about 28% dry solids (DS).

BRIEF DESCRIPTION OF THE DRAWINGS

The accompanying drawings are incorporated into the specification and provide non-limiting illustrations of various embodiments. In the drawings.

DETAILED DESCRIPTION OF THE INVENTION

The present disclosure relates to glucoamylases capable of effectively saccharifying a starch substrate at a pH between about 5.2-5.6, without having to adjust the pH following the liquefaction step.

In some aspects, the embodiments of the present disclosure rely on routine techniques and methods used in the field of genetic engineering and molecular biology. The following resources include descriptions of general methodology useful in accordance with the disclosure: Sambrook et al., MOLECULAR CLONING: A LABORATORY MANUAL (2nd Ed., 1989); Kreigler, GENE TRANSFER AND EXPRESSION; A LABORATORY MANUAL (1990) and Ausubel et al., Eds. CURRENT PROTOCOLS IN MOLECULAR BIOLOGY (1994). Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with a general dictionary of many of the terms used in this disclosure. Although any methods and materials similar or equivalent to those described herein can be used in the practice or testing of the present disclosure, the representative methods and materials are described. Numeric ranges are inclusive of the numbers defining the range. The headings provided herein are not limitations of the various aspects or embodiments, which can be had by reference to the specification as a whole.

1. Definitions and Abbreviations

In accordance with this detailed description, the following abbreviations and definitions apply. It should be noted that as used herein, the singular forms "a," "an," and "the" include plural referents unless the context clearly dictates otherwise. Thus, for example, reference to "an enzyme" includes a plurality of such enzymes.

1.1. Definitions

As used herein, "amino acid sequence" is synonymous with the term "polypeptide" and/or the term "protein." In some instances, the term "amino acid sequence" is synonymous with the term "peptide"; in some instances, the term "amino acid sequence" is synonymous with the term "enzyme."

As used herein, "nucleotide sequence" or "nucleic acid sequence" refers to a sequence of genomic, synthetic, or recombinant origin and may be double-stranded or single-stranded, whether representing the sense or anti-sense strand. As used herein, the term "nucleic acid" may refer to genomic DNA, cDNA, synthetic DNA, or RNA. The residues of a nucleic acid may contain any of the chemically modifications commonly known and used in the art.

"Isolated" means that the material is at least substantially free from at least one other component that the material is naturally associated and found in nature.

"Purified" means that the material is in a relatively pure state, e.g., at least about 90% pure, at least about 95% pure, or at least about 98% pure.

"Oligosaccharide" means a carbohydrate molecule composed of 3-20 monosaccharides.

As used herein, "transformed cell" includes cells that have been transformed by use of recombinant DNA techniques. Transformation typically occurs by insertion of one or more nucleotide sequences into a cell. The inserted nucleotide sequence may be a heterologous nucleotide sequence, i.e., is a sequence that may not be natural to the cell that is to be transformed, such as a fusion protein.

As used herein, "starch" refers to any material comprised of the complex polysaccharide carbohydrates of plants, comprised of amylose and amylopectin with the formula $(C_6H_{10}O_5)_x$, wherein "X" can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

As used herein, "granular starch" refers to uncooked (raw) starch, which has not been subject to gelatinization.

As used herein, "starch gelatinization" means solubilization of a starch molecule to form a viscous suspension.

As used herein, "gelatinization temperature" refers to the lowest temperature at which gelatinization of a starch substrate occurs. The exact temperature depends upon the specific starch substrate and further may depend on the particular variety and the growth conditions of plant species from which the starch is obtained.

"DE" or "dextrose equivalent" is an industry standard for measuring the concentration of total reducing sugars, calculated as the percentage of the total solids that have been converted to reducing sugars. The granular starch that has not been hydrolyzed has a DE that is about zero (0), and D-glucose has a DE of about 100.

As used herein, "starch substrate" refers to granular starch or liquefied starch using refined starch, whole ground grains, or fractionated grains.

As used herein, "liquefied starch" refers to starch that has gone through solubilization process, for example, the conventional starch liquefaction process.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4+ (>DP4) denotes polymers with a degree of polymerization of greater than four.

As used herein, "fermentable sugars" refer to saccharides that are capable of being metabolized under fermentation conditions. These sugars typically refer to glucose, maltose, and maltotriose (DP1, DP2 and DP3).

As used herein, "total sugar content" refers to the total sugar content present in a starch composition.

As used herein, "ds" refers to dissolved solids in a solution.

As used herein, "starch-liquefying enzyme" refers to an enzyme that catalyzes the hydrolysis or breakdown of granular starch. Exemplary starch liquefying enzymes include alpha-amylases (EC 3.2.1.1).

"Amylase" means an enzyme that is, among other things, capable of catalyzing the degradation of starch.

"Alpha-amylases (EC 3.2.1.1)" refer to endo-acting enzymes that cleave α-D-(1→4) O-glycosidic linkages within the starch molecule in a random fashion. In contrast, the exo-acting amylolytic enzymes, such as beta-amylases (EC 3.2.1.2; α-D-(1→4)-glucan maltohydrolase) and some product-specific amylases like maltogenic alpha-amylase (EC 3.2.1.133) cleave the starch molecule from the non-reducing end of the substrate. These enzymes have also been described as those effecting the exo- or endohydrolysis of 1,4-α-D-glucosidic linkages in polysaccharides containing 1,4-α-linked D-glucose units. Another term used to describe these enzymes is glycogenase. Exemplary enzymes include alpha-1,4-glucan 4-glucanohydrolase.

As used herein, "glucoamylases" refer to the amyloglucosidase class of enzymes (EC 3.2.1.3, glucoamylase, α-1,4-D-glucan glucohydrolase). These are exo-acting enzymes that release glucosyl residues from the non-reducing ends of amylose and/or amylopectin molecules. The enzymes are also capably of hydrolyzing α-1, 6 and α-1,3 linkages, however, at much slower rates than the hydrolysis of α-1,4 linkages.

As used herein, "maximum activity" refers to the enzyme activity measured under the most favorable conditions, for example, at an optimum pH. As used herein, "optimum pH" refers to a pH value, under which the enzyme displays the highest activity with other conditions being equal.

The phrase "mature form" of a protein or polypeptide refers to the final functional form of the protein or polypeptide. A mature form of a glucoamylase may lack a signal peptide and/or initiator methionine, for example. A mature form of a glucoamylase may be produced from its native host, for example, by endogenous expression. Alternatively, a mature form of a glucoamylase may be produced from a non-native host, for example, by exogenous expression. An exogenously expressed glucoamylase may have a varied glycosylation pattern compared to the endogenous expressed counterpart.

The term "parent" or "parent sequence" refers to a sequence that is native or naturally occurring.

As used herein, the terms "variant" is used in reference to glucoamylases that have some degree of amino acid sequence identity to a parent glucoamylase sequence. A variant is similar to a parent sequence, but has at least one substitution, deletion or insertion in their amino acid sequence that makes them different in sequence from a parent glucoamylase. In some cases, variants have been manipulated and/or engineered to include at least one substitution, deletion, or insertion in their amino acid sequence that makes them different in sequence from a parent. Additionally, a glucoamylase variant may retain the functional characteristics of the parent glucoamylase, e.g., maintaining a glucoamylase activity that is at least 50%, 60%, 70%, 80%, 90%, 95%, 98%, or 99% of that of the parent glucoamylase.

As used herein, "hydrolysis of starch" refers to the cleavage of glucosidic bonds with the addition of water molecules.

As used herein, "end product" or "desired end product" refers to a molecule or compound to which a starch substrate is converted into, by an enzyme and/or a microorganism.

As used herein, "contacting" or "admixing" refers to the placing of the respective enzyme(s) in sufficiently close proximity to the respective substrate to enable the enzyme(s) to convert the substrate to the end product. Those skilled in the art will recognize that mixing solutions of the enzyme with the respective substrates can affect contacting or admixing.

1.2. Abbreviations

The following abbreviations apply unless indicated otherwise:
AA alpha-amylase
AmyE *Bacillus subtilis* alpha-amylase
AnGA *Aspergillus niger* glucoamylase
cDNA complementary DNA
DE Dextrose Equivalent
DNA deoxyribonucleic acid
DP3 degree of polymerization with three subunits
DPn degree of polymerization with n subunits
DS or ds dry solid
dss dry solid starch
EC enzyme commission for enzyme classification
g gram
GAU glucoamylase units
H-GA *Humicola grisea* glucoamylase
HgGA *Humicola grisea* glucoamylase
HPLC high pressure liquid chromatography
MOPS 3-(N-morpholino)propanesulfonic acid
PEG polyethylene glycol
RNA ribonucleic acid
RO reverse osmosis
TeGA *Talaromyces emersonii* glucoamylase
TrGA *Trichoderma reesei* glucoamylase
μm micrometer 2. Enzymes in Starch Processing
   2.1. Glucoamylase
      2.1.1. Glucoamylases Having the Desired pH Profile Glucoamylases are produced by numerous strains of bacteria, fungi, yeast and plants. Many fungal glucoamylases are fungal enzymes that are extracellularly produced, for example from strains of *Aspergillus* (Svensson et al., *Carlsberg Res. Commun.* 48: 529-544 (1983); Boel et al., *EMBO J.* 3: 1097-1102 (1984); Hayashida et al., *Agric. Biol. Chem.* 53: 923-929 (1989); U.S. Pat. No. 5,024,941; U.S. Pat. No. 4,794, 175 and WO 88/09795); *Talaromyces* (U.S. Pat. No. 4,247, 637; U.S. Pat. No. 6,255,084; and U.S. Pat. No. 6,620,924); *Rhizopus* (Ashikari et al., *Agric. Biol. Chem.* 50: 957-964 (1986); Ashikari et al., *App. Microbio. Biotech.* 32: 129-133 (1989) and U.S. Pat. No. 4,863,864); *Humicola* (WO 05/052148 and U.S. Pat. No. 4,618,579); and *Mucor* (Houghton-Larsen et al., *Appl. Microbiol. Biotechnol.* 62: 210-217 (2003)). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States. In general, glucoamylases may be, and commonly are, used with alpha-amylases in starch hydrolyzing processes to hydrolyze starch to dextrins and then to glucose. The glucose may then be converted to fructose by other enzymes (e.g., glucose isomerases); crystallized; or used in fermentations to produce numerous end products (e.g., ethanol, citric acid, succinic acid, ascorbic acid intermediates, glutamic acid, glycerol, 1,3-propanediol and lactic acid).

The embodiments of the present disclosure utilize a glucoamylase capable of effectively saccharifying a starch substrate at a pH, for example, between 5.2 and 5.6. The glucoamylases having the desired pH profile include, but are not limited to, *Humicola grisea* glucoamylase (HgGA).

HgGA may be the glucoamylase comprising the amino acid sequence of SEQ ID NO: 3, which is described in detail in U.S. Pat. Nos. 4,618,579 and 7,262,041. This HgGA is also described as a granular starch hydrolyzing enzyme (GSHE), because it is capable of hydrolyzing starch in granular form. The genomic sequence coding the HgGA from *Humicola grisea* var. *thermoidea* is presented as SEQ ID NO: 1, which contains three putative introns (positions 233-307, 752-817, and 950-1006). The native HgGA from *Humicola grisea* var. *thermoidea* has the amino acid sequence of SEQ ID NO: 2, which includes a signal peptide containing 30 amino acid residues (positions 1 to 30 of SEQ ID NO: 2). Cleavage of the signal peptide results in the mature HgGA having the amino acid sequence of SEQ ID NO: 3. The embodiments of the present disclosure also include a HgGA produced from a *Trichoderma* host cell, e.g., a *Trichoderma reesei* cell. See U.S. Pat. No. 7,262,041.

2.1.2. Structure and Function

The glucoamylase of the embodiment of the present disclosure may also be a variant of HgGA. The variant has at least 99% sequence identity to the parent glucoamylase. Optionally, the variant has one, two, three, four, five, or six amino acids modification compared to the mature form of the parent glucoamylase. In one embodiment, the glucoamylase is a variant of a parent HgGA comprising SEQ ID NO: 3, where the variant has at least 99% identity to the parent glucoamylase. The variant possesses the desired pH profile and capability of saccharifying a starch substrate at a pH in the range of 5.2 to 5.6. In some embodiments, the variants may possess other improved properties, such as improved thermostability and improved specificity.

Glucoamylases consist of as many as three distinct structural domains: a catalytic domain of approximately 450 residues that is structurally conserved in all glucoamylases, generally followed by a linker region consisting of between 30 and 80 residues that are connected to a starch-binding domain of approximately 100 residues. The structure of the *Trichoderma reesei* glucoamylase (TrGA) with all three regions intact was determined to 1.8 Angstrom resolution. See WO 2009/048488 and WO 2009/048487. Using the determined coordinates, the structure was aligned with the coordinates of the catalytic domain of the glucoamylase from *Aspergillus awamori* strain X100 that was determined previously (Aleshin, A. E., Hoffman, C., Firsov, L. M., and Honzatko, R. B. Refined crystal structures of glucoamylase from *Aspergillus awamori* var. X100. *J. Mol. Biol.* 238: 575-591 (1994)). See id. The structure of the catalytic domains of TrGA and *Aspergillus awamori* glucoamylase overlap very closely, and it is possible to identify equivalent residues based on this structural superposition. See id. It is further believed that all glucoamylases share the basic structure. See id.

Given the well-known structure and function relationship of glucoamylases, glucoamylase variants having altered properties have been successfully created and characterized. The variants may display improved properties as compared to the parent glucoamylases. The improved properties may include, and are not limited to, increased thermostability and increased specific activity. For example, methods for making and characterizing TrGA variants with altered properties have been described in WO 2009/067218. Functional TrGA variants have been identified having one or more specific sequence modifications. Some TrGA variants, for example, have multiple sequence modifications. WO 2009/067218 discloses TrGA variants with six or more amino acid modifications, for example. These TrGA variants show at least as much activity as the parent TrGA, and in many cases show improved properties. It is expected that corresponding residue changes in HgGA will yield variants with glucoamylase activity. The glucoamylase variants useful in the present methods can efficiently hydrolyze starch at a pH in the range of 5.2 to 5.6.

2.1.3. Production of Glucoamylase

Glucoamylases suitable for the embodiments of the present disclosure may be produce with recombinant DNA technology in various host cells.

In some embodiments, the host cells are selected from bacterial, fungal, plant and yeast cells. The term host cell includes both the cells, progeny of the cells and protoplasts created from the cells that are used to produce a variant glucoamylase according to the disclosure. In some embodiments, the host cells are fungal cells and typically filamentous fungal host cells. The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts. Vegetative growth by filamentous fungi is by hyphal elongation and carbon catabolism is obligatory aerobic. In the embodiments of the present disclosure, the filamentous fungal parent cell may be a cell of a species of, but not limited to, *Trichoderma*, (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., (1984) Appl. Microbiol. Biotechnol 20:46-53; ATCC No. 56765 and ATCC No. 26921); *Penicillium* sp.; *Humicola* sp. (e.g., *H. insolens, H. lanuginosa* and *H. grisea*); *Chrysosporium* sp. (e.g., *C. lucknowense*), *Gliocladium* sp., *Aspergillus* sp. (e.g., *A. oryzae, A. niger, A sojae, A. japonicus, A. nidulans*, and *A. awamori*) (Ward et al., (1993) Appl. Microbiol. Biotechnol. 39:738-743 and Goedegebuur et al., (2002) Genet. 41:89-98), *Fusarium* sp., (e.g., *F. roseum, F. graminum F. cerealis, F. oxysporuim* and *F. venenatum*), *Neurospora* sp., (*N. crassa*), *Hypocrea* sp., *Mucor* sp., (*M. miehei*), *Rhizopus* sp. and *Emericella* sp. (see also, Innis et al., (1985) Sci. 228:21-26). The term "*Trichoderma*" or "*Trichoderma* sp." or "*Trichoderma* spp." refers to any fungal genus previously or currently classified as *Trichoderma*. In other embodiments, the host cell will be a genetically engineered host cell wherein native genes have been inactivated, for example by deletion in fungal cells. Where it is desired to obtain a fungal host cell having one or more inactivated genes known methods may be used (e.g., methods disclosed in U.S. Pat. Nos. 5,246,853 and 5,475,101, and WO 92/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, egl1 and egl2 genes will be inactivated and/or typically deleted. Typically, *Trichoderma reesei* host cells having quad-deleted proteins are set forth and described in U.S. Pat. No. 5,847,276 and WO 05/001036. In other embodiments, the host cell is a protease deficient or protease minus strain.

To produce the glucoamylase of the embodiments of the present disclosure with the recombinant DNA technology, a DNA construct comprising nucleic acid encoding the amino acid sequence of the designated glucoamylase can be constructed and transferred into, for example, a *Trichoderma reesei* host cell. The vector may be any vector which when introduced into a *Trichoderma reesei* host cell can be integrated into the host cell genome and can be replicated. Reference is made to the Fungal Genetics Stock Center Catalogue of Strains (FGSC, <www.fgsc.net>) for a list of vectors. Additional examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. The nucleic acid encoding the glucoamylase can be operably linked to a suitable promoter, which shows transcriptional activity in *Trichoderma reesei* host cell. The promoter may be derived from genes encoding proteins either homologous or heterologous to the host cell. Suitable non-limiting examples of promoters include cbh1, cbh2, egl1, egl2. In one embodiment, the promoter may be a native *T. reesei* promoter. Typically, the promoter can be *T. reesei* cbh1, which is an inducible promoter and has been deposited in GenBank under Accession No. D86235. An "inducible promoter" may refer to a promoter that is active under environmental or developmental regulation. In another embodiment, the promoter can be one that is heterologous to *T. reesei* host cell. Other examples of useful promoters include promoters from *A. awamori* and *A. niger* glucoamylase genes (see, e.g., Nunberg et al., (1984) *Mol. Cell Biol.* 4:2306-2315 and Boel et al., (1984) *EMBO J.* 3:1581-1585). Also, the promoters of the *T. reesei* xln1 gene and the cellobiohydrolase 1 gene may be useful.

In some embodiments, the glucoamylase coding sequence can be operably linked to a signal sequence. The signal sequence may be the native signal peptide of the glucoamylase (residues 1-20 of SEQ ID NO: 2 for HgGA, for example). Alternatively, the signal sequence may have at least 90% or at least 95% sequence identity to the native signal sequence. In additional embodiments, a signal sequence and a promoter sequence comprising a DNA construct or vector to be introduced into the *T. reesei* host cell are derived from the same source. For example, in some embodiments, the signal sequence can be the cdh1 signal sequence that is operably linked to a cdh1 promoter.

In some embodiments, the expression vector may also include a termination sequence. In one embodiment, the termination sequence and the promoter sequence can be derived from the same source. In another embodiment, the termination sequence can be homologous to the host cell. A particularly suitable terminator sequence can be cbh1 derived from *T. reesei*. Other exemplary fungal terminators include the terminator from *A. niger* or *A. awamori* glucoamylase gene.

In some embodiments, an expression vector may include a selectable marker. Examples of representative selectable markers include ones that confer antimicrobial resistance (e.g., hygromycin and phleomycin). Nutritional selective markers also find use in the present disclosure including those markers known in the art as amdS, argB, and pyr4. Markers useful in vector systems for transformation of *Trichoderma* are known in the art (see, e.g., Finkelstein, chapter 6 in BIO-TECHNOLOGY OF FILAMENTOUS FUNGI, Finkelstein et al. Eds. Butterworth-Heinemann, Boston, Mass. (1992), Chap. 6.; and Kinghorn et al. (1992) APPLIED MOLECULAR GENETICS OF FILAMENTOUS FUNGI, Blackie Academic and Professional, Chapman and Hall, London). In a representative embodiment, the selective marker may be the amdS gene, which encodes the enzyme acetamidase, allowing transformed cells to grow on acetamide as a nitrogen source. The use of *A. nidulans* amdS gene as a selective marker is described for example in Kelley et al., (1985) *EMBO J.* 4:475-479 and Penttila et al., (1987) *Gene* 61:155-164.

An expression vector comprising a DNA construct with a polynucleotide encoding the glucoamylase may be any vector which is capable of replicating autonomously in a given fungal host organism or of integrating into the DNA of the host. In some embodiments, the expression vector can be a plasmid. In typical embodiments, two types of expression vectors for obtaining expression of genes are contemplated.

The first expression vector may comprise DNA sequences in which the promoter, glucoamylase-coding region, and terminator all originate from the gene to be expressed. In some embodiments, gene truncation can be obtained by deleting undesired DNA sequences (e.g., DNA encoding unwanted domains) to leave the domain to be expressed under control of its own transcriptional and translational regulatory sequences.

The second type of expression vector may be preassembled and contains sequences needed for high-level transcription and a selectable marker. In some embodiments, the coding region for the glucoamylase gene or part thereof can be inserted into this general-purpose expression vector such that it is under the transcriptional control of the expression construct promoter and terminator sequences. In some embodiments, genes or part thereof may be inserted downstream of a strong promoter, such as the strong cbh1 promoter.

Methods used to ligate the DNA construct comprising a polynucleotide encoding the glucoamylase, a promoter, a terminator and other sequences and to insert them into a suitable vector are well known in the art Linking can be generally accomplished by ligation at convenient restriction sites. If such sites do not exist, the synthetic oligonucleotide linkers are used in accordance with conventional practice. (see, Sambrook (1989) supra, and Bennett and Lasure, MORE GENE MANIPULATIONS IN FUNGI, Academic Press, San Diego (1991) pp 70-76.). Additionally, vectors can be constructed using known recombination techniques (e.g., Invitrogen Life Technologies, Gateway Technology).

Introduction of a DNA construct or vector into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al., (1987), supra, chapter 9; and Sambrook (1989) supra, and Campbell et al., (1989) *Curr. Genet.* 16:53-56). The expression of heterologous protein in *Trichoderma* is described in U.S. Pat. Nos. 6,022,725; 6,268,328; Harkki et al. (1991); *Enzyme Microb. Technol.* 13:227-233; Harkki et al., (1989) *Bio Technol.* 7:596-603; EP 244,234; EP 215,594; and Nevalainen et al., "The Molecular Biology of *Trichoderma* and its Application to the Expression of Both Homologous and Heterologous Genes," in MOLECULAR INDUSTRIAL MYCOLOGY, Eds. Leong and Berka, Marcel Dekker Inc., NY (1992) pp. 129-148).

In some embodiments, genetically stable transformants can be constructed with vector systems whereby the nucleic acid encoding glucoamylase is stably integrated into a host strain chromosome. Transformants are then purified by known techniques.

In one non-limiting example, stable transformants including an amdS marker are distinguished from unstable transformants by their faster growth rate and the formation of circular colonies with a smooth, rather than ragged outline on solid culture medium containing acetamide. Additionally, in some cases a further test of stability can be conducted by growing the transformants on solid non-selective medium (i.e., medium that lacks acetamide), harvesting spores from this culture medium and determining the percentage of these spores which subsequently germinate and grow on selective medium containing acetamide. Alternatively, other methods known in the art may be used to select transformants.

Uptake of DNA into the host *Trichoderma* sp. strain is dependent upon the calcium ion concentration. Generally, between about 10 mM $CaCl_2$ and 50 mM $CaCl_2$ may be used in an uptake solution. Besides the need for the calcium ion in the uptake solution, other compounds generally included are a buffering system such as TE buffer (10 mM Tris, pH 7.4; 1 mM EDTA) or 10 mM MOPS, pH 6.0 buffer (morpholinepropanesulfonic acid) and polyethylene glycol (PEG). It is believed that the polyethylene glycol acts to fuse the cell membranes, thus permitting the contents of the medium to be delivered into the cytoplasm of the *Trichoderma* sp. strain and the plasmid DNA is transferred to the nucleus. This fusion frequently leaves multiple copies of the plasmid DNA integrated into the host chromosome.

Usually a suspension containing the *Trichoderma* sp. protoplasts or cells that have been subjected to a permeability treatment at a density of $10^5$ to $10^7$/mL, typically, $2 \times 10^6$/mL are used in transformation. A volume of 100 µL of these protoplasts or cells in an appropriate solution (e.g., 1.2 M sorbitol; 50 mM $CaCl_2$) are mixed with the desired DNA. Generally, a high concentration of PEG may be added to the uptake solution. From 0.1 to 1 volume of 25% PEG 4000 can be added to the protoplast suspension. It is also typical to add about 0.25 volumes to the protoplast suspension. Additives such as dimethyl sulfoxide, heparin, spermidine, potassium chloride and the like may also be added to the uptake solution and aid in transformation. Similar procedures are available for other fungal host cells. See, e.g., U.S. Pat. Nos. 6,022,725 and 6,268,328.

Generally, the mixture can be then incubated at approximately 0° C. for a period of between 10 to 30 minutes. Additional PEG may then be added to the mixture to further enhance the uptake of the desired gene or DNA sequence. The 25% PEG 4000 can be generally added in volumes of 5 to 15 times the volume of the transformation mixture; however, greater and lesser volumes may be suitable. The 25% PEG 4000 may be typically about 10 times the volume of the transformation mixture. After the PEG is added, the transformation mixture can then be incubated either at room temperature or on ice before the addition of a sorbitol and $CaCl_2$ solution. The protoplast suspension can then be further added to molten aliquots of a growth medium. This growth medium permits the growth of transformants only.

Generally, cells are cultured in a standard medium containing physiological salts and nutrients (see, e.g., Pourquie, J. et al., BIOCHEMISTRY AND GENETICS OF CELLULOSE DEGRADATION, eds. Aubert, J. P. et al., Academic Press, pp. 7186, 1988 and Ilmen, M. et al., (1997) *Appl. Environ. Microbiol.* 63:1298-1306). Common commercially prepared media (e.g., Yeast Malt Extract (YM) broth, Luria Bertani (LB) broth and Sabouraud Dextrose (SD) broth also find use in the present embodiments.

Culture-conditions are also standard, e.g., cultures are incubated at approximately 28° C. in appropriate medium in shake cultures or fermentors until desired levels of glucoamylase expression are achieved. After fungal growth has been established, the cells are exposed to conditions effective to cause or permit the expression of the glucoamylase. In cases where the glucoamylase coding sequence is under the control of an inducible promoter, the inducing agent (e.g., a sugar, metal salt or antimicrobial), can be added to the medium at a concentration effective to induce glucoamylase expression.

In general, the glucoamylase produced in cell culture may be secreted into the medium and may be purified or isolated, e.g., by removing unwanted components from the cell culture medium. In some cases, the glucoamylase can be produced in a cellular form, necessitating recovery from a cell lysate. In such cases, the enzyme may be purified from the cells in which it was produced using techniques routinely employed by those of skill in the art. Examples of these techniques include, but are not limited to, affinity chromatography (Tilbeurgh et al., (1984) *FEBS Lett.* 16: 215), ion-exchange chromatographic methods (Goyal et al., (1991) *Biores. Technol.* 36: 37; Fliess et al., (1983) *Eur. J. Appl. Microbiol. Biotechnol.* 17: 314; Bhikhabhai et al, (1984) *J. Appl. Biochem.* 6: 336; and Ellouz et al., (1987) *Chromatography* 396: 307), including ion-exchange using materials with high resolution power (Medve et al., (1998) *J. Chromatography A* 808: 153), hydrophobic interaction chromatography (see, Tomaz and Queiroz, (1999) *J. Chromatography A* 865: 123; two-phase partitioning (see, Brumbauer, et al., (1999) *Bioseparation* 7: 287); ethanol precipitation; reverse phase HPLC, chromatography on silica or on a cation-exchange resin such as DEAE, chromatofocusing, SDS-PAGE, ammonium sulfate precipitation, and gel filtration (e.g., Sephadex G-75).

2.2. Alpha-Amylases

Alpha-amylases constitute a group of enzymes present in microorganisms and tissues from animals and plants. They are capable of hydrolyzing alpha-1,4-glucosidic bonds of glycogen, starch, related polysaccharides, and some oligosaccharides. Although all alpha-amylases possess the same catalytic function, their amino acid sequences vary greatly. The sequence identity between different amylases can be virtually non-existent, e.g., falling below 25%. Despite considerable amino acid sequence variation, alpha-amylases share a common overall topological scheme that has been identified after the three-dimensional structures of alpha-amylases from different species have been determined. The common three-dimensional structure reveals three domains: (1) a "TIM" barrel known as domain A, (2) a long loop region known as domain B that is inserted within domain A, and (3) a region close to the C-terminus known as domain C that contains a characteristic beta-structure with a Greek-key motif.

"Termamyl-like" alpha-amylases refer to a group of alpha-amylases widely used in the starch-processing industry. The *Bacillus licheniformis* alpha-amylase having an amino acid sequence of SEQ ID NO: 2 of U.S. Pat. No. 6,440,716 is commercially available as Termamyl®. Termamyl-like alpha-amylases commonly refer to a group of highly homologous alpha-amylases produced by *Bacillus* spp. Other members of the group include the alpha-amylases from *Geobacillus stearothermophilus* (previously known as *Bacillus stearothermophilus*; both names are used interchangeably in the present disclosure) and *Bacillus amyloliquefaciens*, and those derived from *Bacillus* sp. NCIB 12289, NCIB 12512, NCIB 12513, and DSM 9375, all of which are described in detail in U.S. Pat. No. 6,440,716 and WO 95/26397.

Although alpha-amylases universally contain the three domains discussed above, the three-dimensional structures of some alpha-amylases, such as AmyE from *Bacillus subtilis*, differ from Termamyl-like alpha-amylases. These enzymes are collectively referred as non-Termamyl-like alpha-amylases. "AmyE" for the purpose of this disclosure means a naturally occurring alpha-amylase (EC 3.2.1.1; 1,4-α-D-glucan glucanohydrolase) from *Bacillus subtilis*. Representative AmyE enzymes and the variants thereof are disclosed in U.S. patent application Ser. No. 12/478,266 and Ser. No. 12/478, 368, both filed Jun. 4, 2009, and Ser. No. 12/479,427, filed Jun. 5, 2009.

2.3. Other Enzymes

In embodiments of the present disclosure, other enzyme(s) may also be supplemented in starch processing, during saccharification and/or fermentation. These supplementary enzymes may include proteases, pullulanases, isoamylases, cellulases, hemicellulases, xylanases, cyclodextrin glycotransferases, lipases, phytases, laccases, oxidases, esterases, cutinases, xylanases, pullulanases, and/or alpha-glucosidases. See, e.g., WO 2009/099783. Skilled artisans in the art are well aware of the methods using the above-listed enzymes.

3. Starch Processing

3.1. Starch Substrates and Raw Materials

Those of skill in the art are well aware of available methods that may be used to prepare starch substrates for use in the processes disclosed herein. For example, a useful starch substrate may be obtained from tubers, roots, stems, legumes, cereals, or whole grain. More specifically, the granular starch comes from plants that produce high amounts of starch. For example, granular starch may be obtained from corn, wheat, barley, rye, milo, sago, cassava, tapioca, sorghum, rice, peas, bean, banana, or potatoes. Corn contains about 60-68% starch; barley contains about 55-65% starch; millet contains about 75-80% starch; wheat contains about 60-65% starch; and polished rice contains about 70-72% starch. Specifically contemplated starch substrates are cornstarch, wheat starch, and barley starch. The starch from a grain may be ground or whole and includes corn solids, such as kernels, bran and/or cobs. The starch may be highly refined raw starch or feedstock from starch refinery processes. Various starches also are commercially available. For example, cornstarch may be available from Cerestar, Sigma, and Katayama Chemical Industry Co. (Japan); wheat starch may be available from Sigma; sweet potato starch may be available from Wako Pure Chemical Industry Co. (Japan); and potato starch may be available from Nakaari Chemical Pharmaceutical Co. (Japan).

3.2. Milling

The starch substrate can be a crude starch from milled whole grain, which contains non-starch fractions, e.g., germ residues and fibers. Milling may comprise either wet milling or dry milling. In wet milling, whole grain can be soaked in water or dilute acid to separate the grain into its component parts, e.g., starch, protein, germ, oil, kernel fibers. Wet milling efficiently separates the germ and meal (i.e., starch granules and protein) and can be particularly suitable for production of syrups. In dry milling, whole kernels are ground into a fine powder and processed without fractionating the grain into its component parts. Dry milled grain thus will comprise significant amounts of non-starch carbohydrate compounds, in addition to starch. Most ethanol comes from dry milling. Alternatively, the starch to be processed may be a highly refined starch quality, for example, at least about 90%, at least about 95%, at least about 97%, or at least about 99.5% pure.

3.3. Gelatinization and Liquefaction

As used herein, the term "liquefaction" or "liquefy" means a process by which starch is converted to less viscous and soluble shorter chain dextrins. This process involves gelatinization of starch simultaneously with or followed by the addition of alpha-amylases. Additional liquefaction-inducing enzymes, e.g., a phytase, optionally may be added.

In some embodiments, the starch substrate prepared as described above may be slurried with water. The starch slurry may contain starch as a weight percent of dry solids of about 10-55%, about 20-45%, about 30-45%, about 30-40%, or about 30-35%. To optimize alpha-amylase stability and activity, the pH of the slurry may be adjusted to the optimal pH for the alpha-amylases. Alpha-amylases remaining in the slurry following liquefaction may be deactivated by lowering pH in a subsequent reaction step or by removing calcium from the slurry.

The slurry of starch plus the alpha-amylases may be pumped continuously through a jet cooker, which may be steam heated from about 85° C. to up to about 105° C. Gelatinization occurs very rapidly under these conditions, and the enzymatic activity, combined with the significant shear forces, begins the hydrolysis of the starch substrate. The residence time in the jet cooker can be very brief. The partly gelatinized starch may be passed into a series of holding tubes maintained at about 85-105° C. and held for about 5 min. to complete the gelatinization process. These tanks may contain baffles to discourage back mixing. As used herein, the term "secondary liquefaction" refers the liquefaction step subsequent to primary liquefaction, when the slurry is allowed to cool to room temperature. This cooling step can be about 30 minutes to about 180 minutes, e.g., about 90 minutes to 120 minutes. Milled and liquefied grain is also known as mash.

3.4. Saccharification

Following liquefaction, the mash can be further hydrolyzed through saccharification to high density glucose syrups that can be readily used in the downstream applications. The saccharification of the present embodiments can be carried out at a pH in the range of 5.2 to 5.6, by using a glucoamylase as described above. The glucoamylase may be dosed at the range of about 0.15 to 2.0 GAU/g dss, about 0.20 to 1.5 GAU/g dss, or 1.0 to 1.5 GAU/g dss. The saccharification may be performed at about 58° C. to about 62° C.

A full saccharification step may typically range 24 to 96 hours, 24 to 72 hours, or 24 to 48 hours.

3.5. Fermentation

In some embodiments of the present disclosure, the fermentable sugars may be subject to batch or continuous fermentation conditions. A classical batch fermentation is a closed system, wherein the composition of the medium is set at the beginning of the fermentation and is not subject to artificial alterations during the fermentation. Thus, at the beginning of the fermentation the medium may be inoculated with the desired organism(s). In this method, fermentation can be permitted to occur without the addition of any components to the system. Typically, a batch fermentation qualifies as a "batch" with respect to the addition of the carbon source and attempts are often made at controlling factors such as pH and oxygen concentration. The metabolite and biomass compositions of the batch system change constantly up to the time the fermentation is stopped. Within batch cultures, cells progress through a static lag phase to a high growth log phase, and finally to a stationary phase where growth rate is diminished or halted. If untreated, cells in the stationary phase eventually die. In general, cells in log phase are responsible for the bulk of production of the end product.

A variation on the standard batch system is the "fed-batch fermentation" system, which may be used in some embodiments of the present disclosure. In this variation of a typical batch system, the substrate can be added in increments as the fermentation progresses. Fed-batch systems are particularly useful when catabolite repression is apt to inhibit the metabolism of the cells and where it is desirable to have limited amounts of substrate in the medium. Measurement of the actual substrate concentration in fed-batch systems may be difficult and is therefore estimated on the basis of the changes of measurable factors such as pH, dissolved oxygen and the partial pressure of waste gases such as $CO_2$. Both batch and fed-batch fermentations are common and well known in the art.

On the other hand, continuous fermentation is an open system where a defined fermentation medium can be added continuously to a bioreactor and an equal amount of conditioned medium can be removed simultaneously for processing. Continuous fermentation generally maintains the cultures at a constant high density where cells are primarily in log phase growth. Continuous fermentation allows for the modulation of one factor or any number of factors that affect cell growth and/or end product concentration. For example, in one embodiment, a limiting nutrient such as the carbon source or nitrogen source can be maintained at a fixed rate while all other parameters are allowed to moderate. In other systems, a number of factors affecting growth can be altered continuously while the cell concentration, measured by media turbidity, may be kept constant. Continuous systems strive to maintain steady state growth conditions. Thus, cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology.

In further embodiments, by use of appropriate fermenting microorganisms as known in the art, the fermentation end product may include without limitation alcohol, 1,3-propanediol, succinic acid, lactic acid, amino acids, proteins, functional oligosaccharides, and derivatives thereof. See e.g., WO 2008/086811 (methanol, ethanol, propanol, and butanol fermentation); WO 2003/066816, U.S. Pat. Nos. 5,254,467 and 6,303,352 (1,3-propanediol fermentation); U.S. Pat. Nos. RE 37,393, 6,265,190, and 6,596,521 (succinic acid fermentation); U.S. Pat. No. 5,464,760, WO 2003/095659, Mercier et al., *J. Chem. Tech. Biotechnol.* 55: 111-121, Zhang and Cheryan, *Biotechnol. Lett.* 13: 733-738 (1991), Linko and Javanainen, *Enzyme Microb. Technol.* 19: 118-123 (1996), and Tsai and Moon, *Appl. Biochem. Biotechnol.* 70-72: 417-428 (1998) (lactic acid fermentation); U.S. Pat. Nos. 7,320,882, 7,332,309, 7,666,634, and Zhang et al., *Appl. Microbiol. Biotechnol.* 77: 355-366 (2007) (fermentation of various amino acids).

The above enumerated list are only examples, and one skilled in the art will be aware of a number of fermenting microorganisms that may be appropriately used to obtain a desired end product.

TABLE 1

Composition of Sugars During Saccharification.

| | HgGA dose, GAU/g ds | Time, hours | % of Sugars, 60° C., pH 5.6 | | | |
| --- | --- | --- | --- | --- | --- | --- |
| | | | DP1 | DP2 | DP3 | Higher Sugars |
| 1 | 0.18 | 6.5 | 58.24 | 16.19 | 3.14 | 22.42 |
| 2 | 0.16 | 6.5 | 54.07 | 16.58 | 4.74 | 24.61 |
| 3 | 0.14 | 6.5 | 49.79 | 16.73 | 6.59 | 26.88 |
| 1 | 0.18 | 21 | 81.97 | 7.07 | 1.60 | 9.36 |
| 2 | 0.16 | 21 | 79.10 | 8.42 | 1.55 | 10.93 |
| 3 | 0.14 | 21 | 74.09 | 10.59 | 1.31 | 14.00 |
| 1 | 0.18 | 28 | 88.10 | 4.50 | 1.84 | 5.56 |
| 2 | 0.16 | 28 | 85.60 | 5.50 | 1.82 | 7.08 |
| 3 | 0.14 | 28 | 80.83 | 7.38 | 1.64 | 10.15 |
| 1 | 0.18 | 44.5 | 93.56 | 2.57 | 1.78 | 2.09 |
| 2 | 0.16 | 44.5 | 92.50 | 2.88 | 1.96 | 2.65 |
| 3 | 0.14 | 44.5 | 90.04 | 3.65 | 2.16 | 4.15 |
| 1 | 0.18 | 52 | 94.44 | 2.38 | 1.59 | 1.58 |
| 2 | 0.16 | 52 | 93.71 | 2.53 | 1.83 | 1.93 |
| 3 | 0.14 | 52 | 92.00 | 2.98 | 2.14 | 2.87 |
| 1 | 0.18 | 69.5 | 95.16 | 2.48 | 1.21 | 1.15 |
| 2 | 0.16 | 69.5 | 94.94 | 2.36 | 1.41 | 1.28 |
| 3 | 0.14 | 69.5 | 94.12 | 2.40 | 1.83 | 1.65 |

When HgGA was used at the dose of 0.18 GAU/g ds for saccharification of the liquefact without pH adjustment and in the presence of the pullulanase, the DP1 content reached 88% after 28 hours of incubation, while the content of higher sugars decreased to 5.6%. After 44.5 hours, the DP1 content increased to 93.6%, and the higher sugar content decreased to about 2%. The DP1 concentration achieved after 69.5 hours was 95.2%, whereas the higher sugars were only 1.15%. The data in Table 1 indicate that HgGA can be effective to hydrolyze solubilized starch to glucose in a single pH process.

EXAMPLES

Example 1

Single pH Liquefaction and Saccharification Using *Humicola grisea* Glucoamylase The ability of the *Humicola grisea* glucoamylase (HgGA) to hydrolyze starch substrate (liquefact) at the pH of 5.6, without pH adjustment was evaluated. Corn starch was liquefied by following a conventional bench cooking process using CLEARFLOW® AA (Danisco US Inc., Genencor Division) to obtain a liquefact having DE 10. The liquefact (35% DS) was placed "as is" in 50 ml glass flasks, without pH adjustment to inactivate the α-amylase present in the liquefact (i.e., α-alive liquefact). Saccharification of the liquefact was carried out using HgGA in the presence of OPTIMAX® L-1000 pullulanase (1129 ASPU/g), by incubating the glass flasks at 60° C. in water bath for 69.5 hours. HgGA was used at the following doses: 0.18 GAU/g ds, 0.16 GAU/g ds, and 0.14 GAU/g ds. 0.5 ml samples of the saccharification reaction mixtures were withdrawn at different time intervals, combined with 4.5 ml of RO water, and filtered through 0.2 μm Whatman filters. The samples were then put into vials and subjected to HPLC analysis. The HPLC analysis was conducted using a Rezex RCM-Monosaccharide column and a Bio-Rad® deashing guard column. The composition of various sugars in the saccharification reaction mixtures is presented in Table 1.

Example 2

Single pH Liquefaction and Saccharification Using *Humicola grisea* Glucoamylase and Comparison The ability of HgGA to hydrolyze starch liquefact without pH adjustment was evaluated at the pH of 5.35. HgGA's performance during the single-pH process (α-live) was compared to its ability to hydrolyze starch liquefact when the pH of the liquefact was adjusted (α-killed) before the saccharification step. Corn starch liquefact (12.15 DE, 32% ds) was prepared by conventional bench cooking process using SPEZYME® FRED (Danisco US Inc., Genencor Division).

For the single-pH saccharification (α-live), the liquefact was placed in 50 ml glass flasks "as is," without any pH adjustment, and dosed with enzymes. The enzymes used were either HgGA at the dosages specified in Table 2, or HgGA at the same dosages and in the presence of a pullulanase (OPTIMA® L-1000 pullulanase, 1129 ASPU/g). For the non-single pH saccharification (α-killed), the liquefact was placed in 50 ml flasks and its pH was adjusted to between about 3.5 and 4.0 to kill the α-amylase activity. The liquefact pH was then increased back to 5.35 for saccharification as a control. Enzymes were added to each flask containing the liquefact, as presented in Table 2. Saccharification reaction was carried out by incubating the flasks at 60° C. in water bath for 75.3 hours. 0.5 ml samples of the reaction mixtures were withdrawn at different time intervals, diluted by combining with 4.5 ml of RO water, and filtered through 0.2 μm Whatman filters. The samples were then placed in vials for HPLC analysis. The HPLC analysis was conducted using a Rezex RCM-Monosaccharide column with a Bio-Rad® deashing guard column. The composition of various sugars in the saccharification reaction mixtures is presented in Table 2.

TABLE 2

Composition of Sugars During Saccharification (HgGA).

| Flask | Enzyme doses (HgGA, GAU/g ds) | Time, hours | DP1 | DP2 | DP3 | Higher Sugars |
|---|---|---|---|---|---|---|
| | | % of Sugars, 60° C., pH 5.35 | | | | |
| | α-Live | | | | | |
| 1 | HgGA 0.15 | 7.2 | 63.65 | 15.69 | 1.17 | 19.49 |
| 2 | HgGA 0.20 | 7.2 | 70.30 | 12.04 | 0.99 | 16.66 |
| 3 | HgGA 0.15 + PU | 7.2 | 64.13 | 16.15 | 1.32 | 18.41 |
| 4 | HgGA 0.20 + PU | 7.2 | 70.42 | 12.60 | 1.07 | 15.91 |
| | α-Killed | | | | | |
| 5 | HgGA 0.15 | 6 | 63.32 | 9.98 | 0.85 | 25.84 |
| 6 | HgGA 0.20 | 6 | 70.01 | 7.19 | 0.77 | 22.04 |
| 7 | HgGA 0.15 + PU | 6 | 65.09 | 10.94 | 0.96 | 23.01 |
| 8 | HgGA 0.20 + PU | 6 | 71.68 | 8.26 | 1.01 | 19.06 |
| | α-Live | | | | | |
| 1 | HgGA 0.15 | 18.3 | 82.34 | 6.41 | 1.78 | 9.48 |
| 2 | HgGA 0.20 | 18.3 | 88.09 | 3.92 | 1.93 | 6.06 |
| 3 | HgGA 0.15 + PU | 18.3 | 83.55 | 7.00 | 2.06 | 7.39 |
| 4 | HgGA 0.20 + PU | 18.3 | 88.80 | 4.40 | 2.18 | 4.63 |
| | α-Killed | | | | | |
| 5 | HgGA 0.15 | 17 | 84.33 | 2.62 | 0.88 | 12.18 |
| 6 | HgGA 0.20 | 17 | 88.83 | 2.04 | 0.83 | 8.30 |
| 7 | HgGA 0.15 + PU | 17 | 88.11 | 3.25 | 1.15 | 7.50 |
| 8 | HgGA 0.20 + PU | 17 | 92.04 | 2.48 | 1.08 | 4.40 |
| | α-Live | | | | | |
| 1 | HgGA 0.15 | 27.3 | 88.80 | 3.72 | 2.14 | 5.34 |
| 2 | HgGA 0.20 | 27.3 | 92.17 | 2.68 | 1.86 | 3.29 |
| 3 | HgGA 0.15 + PU | 27.3 | 90.12 | 4.13 | 2.38 | 3.37 |
| 4 | HgGA 0.20 + PU | 27.3 | 93.03 | 2.85 | 1.99 | 2.13 |
| | α-Killed | | | | | |
| 5 | HgGA 0.15 | 26 | 89.74 | 1.99 | 0.74 | 7.53 |
| 6 | HgGA 0.20 | 26 | 92.64 | 2.11 | 0.62 | 4.63 |
| 7 | HgGA 0.15 + PU | 26 | 93.11 | 2.32 | 0.96 | 3.60 |
| 8 | HgGA 0.20 + PU | 26 | 94.70 | 2.27 | 0.81 | 2.22 |
| | α-Live | | | | | |
| 1 | HgGA 0.15 | 33.3 | 90.90 | 3.00 | 2.11 | 3.99 |
| 2 | HgGA 0.20 | 33.3 | 93.37 | 2.48 | 1.68 | 2.47 |
| 3 | HgGA 0.15 + PU | 33.3 | 92.16 | 3.28 | 2.27 | 2.29 |
| 4 | HgGA 0.20 + PU | 33.3 | 94.02 | 2.58 | 1.75 | 1.65 |
| | α-Killed | | | | | |
| 5 | HgGA 0.15 | 32 | 91.52 | 2.02 | 0.73 | 5.74 |
| 6 | HgGA 0.20 | 32 | 93.71 | 2.29 | 0.59 | 3.41 |
| 7 | HgGA 0.15 + PU | 32 | 94.31 | 2.24 | 0.90 | 2.55 |
| 8 | HgGA 0.20 + PU | 32 | 95.08 | 2.38 | 0.73 | 1.81 |
| | α-Live | | | | | |
| 1 | HgGA 0.15 | 43.3 | 92.78 | 2.55 | 1.92 | 2.76 |
| 2 | HgGA 0.20 | 43.3 | 94.34 | 2.51 | 1.41 | 1.74 |
| 3 | HgGA 0.15 + PU | 43.3 | 93.81 | 2.67 | 1.94 | 1.58 |
| 4 | HgGA 0.20 + PU | 43.3 | 94.82 | 2.52 | 1.40 | 1.26 |
| | α-Killed | | | | | |
| 5 | HgGA 0.15 | 42 | 93.33 | 2.18 | 0.56 | 3.94 |
| 6 | HgGA 0.20 | 42 | 94.49 | 2.59 | 0.51 | 2.41 |
| 7 | HgGA 0.15 + PU | 42 | 95.01 | 2.33 | 0.74 | 1.92 |
| 8 | HgGA 0.20 + PU | 42 | 95.18 | 2.61 | 0.60 | 1.61 |
| | α-Live | | | | | |
| 1 | HgGA 0.15 | 51.3 | 93.43 | 2.53 | 1.75 | 2.29 |
| 2 | HgGA 0.20 | 51.3 | 94.75 | 2.61 | 1.23 | 1.41 |
| 3 | HgGA 0.15 + PU | 51.3 | 94.43 | 2.52 | 1.68 | 1.37 |
| 4 | HgGA 0.20 + PU | 51.3 | 95.12 | 2.58 | 1.17 | 1.13 |
| | α-Killed | | | | | |
| 5 | HgGA 0.15 | 50 | 93.94 | 2.38 | 0.58 | 3.09 |
| 6 | HgGA 0.20 | 50 | 94.58 | 2.84 | 0.55 | 2.02 |
| 7 | HgGA 0.15 + PU | 50 | 95.15 | 2.46 | 0.70 | 1.69 |
| 8 | HgGA 0.20 + PU | 50 | 95.04 | 2.84 | 0.66 | 1.45 |
| | α-Live | | | | | |
| 1 | HgGA 0.15 | 67.3 | 94.37 | 2.53 | 1.47 | 1.64 |
| 2 | HgGA 0.20 | 67.3 | 95.32 | 2.90 | 1.00 | 0.78 |
| 3 | HgGA 0.15 + PU | 67.3 | 94.89 | 2.59 | 1.31 | 1.21 |
| 4 | HgGA 0.20 + PU | 67.3 | 95.22 | 2.86 | 0.92 | 1.00 |
| | α-Killed | | | | | |
| 5 | HgGA 0.15 | 66 | 95.26 | 2.30 | 0.35 | 2.09 |
| 6 | HgGA 0.20 | 66 | 94.38 | 3.28 | 0.64 | 1.69 |
| 7 | HgGA 0.15 + PU | 66 | 95.06 | 2.76 | 0.73 | 1.45 |
| 8 | HgGA 0.20 + PU | 66 | 94.72 | 3.25 | 0.70 | 1.33 |
| | α-Live | | | | | |
| 1 | HgGA 0.15 | 75.3 | 94.71 | 2.59 | 1.30 | 1.40 |
| 2 | HgGA 0.20 | 75.3 | 95.28 | 2.98 | 0.85 | 0.89 |
| 3 | HgGA 0.15 + PU | 75.3 | 95.40 | 2.61 | 1.16 | 0.83 |
| 4 | HgGA 0.20 + PU | 75.3 | 95.59 | 2.96 | 0.80 | 0.65 |
| | α-Killed | | | | | |
| 5 | HgGA 0.15 | 74 | 94.53 | 2.87 | 0.57 | 2.04 |
| 6 | HgGA 0.20 | 74 | 94.28 | 3.46 | 0.63 | 1.63 |
| 7 | HgGA 0.15 + PU | 74 | 95.04 | 2.88 | 0.67 | 1.41 |
| 8 | HgGA 0.20 + PU | 74 | 94.63 | 3.40 | 0.66 | 1.32 |

Figure 1:
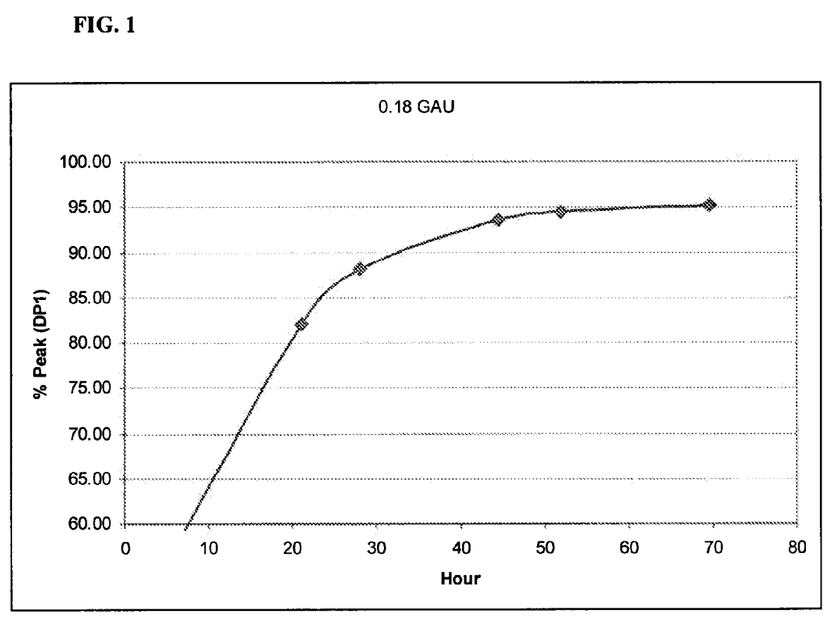
FIG. 1 depicts the time course of accumulated glucose (DP1) concentrations during saccharification process. The single-pH saccharification was carried out using HgGA at the dose of 0.18 glucoamylase units (GAU) per gram of dry substance starch, as described in Example 1 and Table 1.
Figure 2:
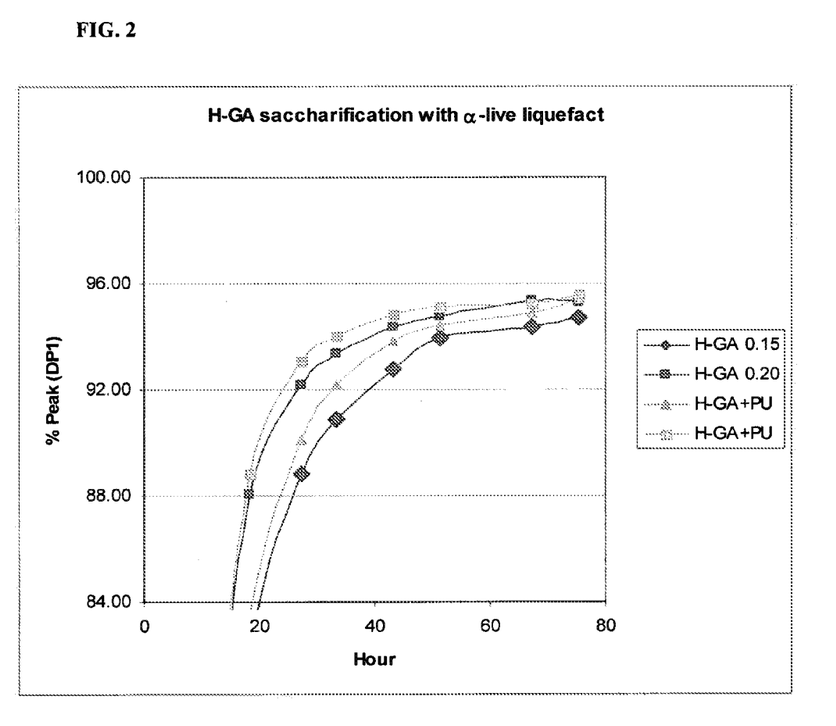
FIG. 2 depicts the time course of accumulated DP1 concentrations during a single-pH α-live) saccharification process. The saccharification was carried out with HgGA or HgGA in the presence of the pullulanase, using enzyme concentrations and under the conditions as described in Example 2 and Table 2 (flasks 1-4).
Figure 3:
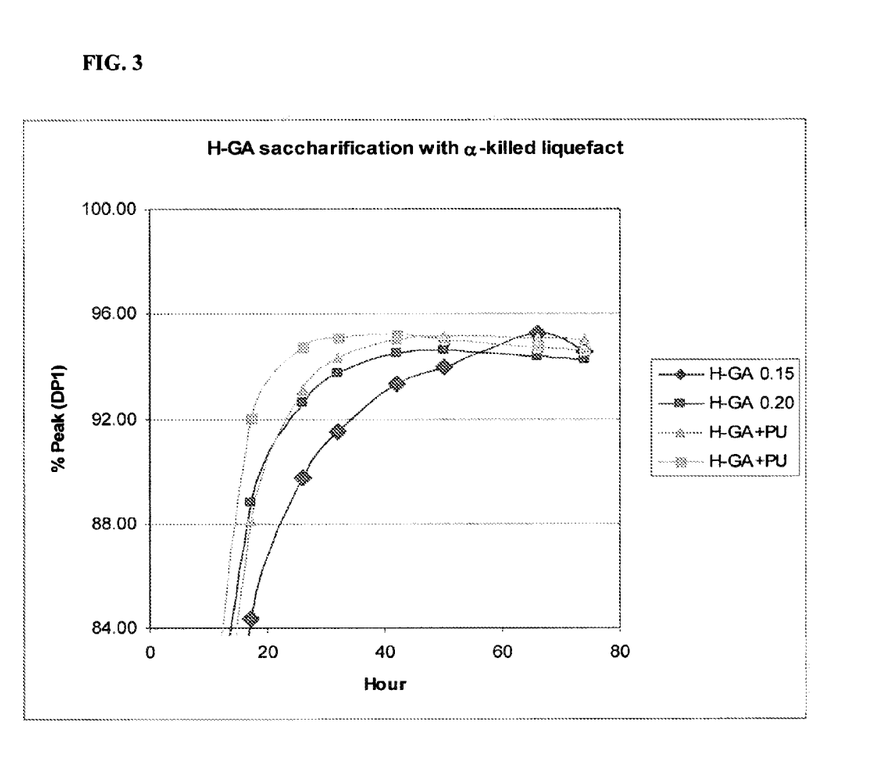
FIG. 3 depicts the time course of accumulated DP1 concentrations during a saccharification process where the α-amylase was inactivated by lowering the liquefact pH to below 4.0 prior to saccharification (α-killed). The saccharification was carried out with HgGA or HgGA in the presence of the pullulanase, using enzyme concentrations and under the conditions described in Example 2 and Table 2 (flasks 5-8).

When saccharification was carried out without pH adjustment using HgGA at the dose of 0.20 GAU/g ds in the presence of the pullulanase, the DP1 content achieved after 27.3 hours was 93%, while the content of higher sugars decreased to 2.13%. After 75.3 hours of saccharification, the DP1 content increased to 95.6%, and the higher sugar content decreased to 0.65%. The data in Table 2 indicate that, when HgGA was used in the single pH process, its performance (e.g., DP1 and DP2 concentrations achieved) was comparable to HgGA's performance in the α-killed process (see FIG. 2 and FIG. 3).

Example 3

Single pH Granular Starch Using *Humicola grisea* Glucoamylase

The ability of the HgGA to hydrolyze granular starch at pH 5.5, without pH adjustment was evaluated. Corn starch was liquefied and saccharified simultaneously in the presence of SPEZYME™ XTRA and HgGA. 28% DS of granular corn starch slurries were prepared in glass flaks and placed in a 60° C. waterbath with the pH adjusted to pH 5.5. Simultaneous liquefaction and saccharification of the granular starch was carried out using HgGA (0.2 GAU/g ds, 0.25 GAU/g ds, 0.3 GAU/g ds) and 2 AAU/g ds of SPEZYME™ XTRA, by incubating the glass flasks at 60° C. in the water bath for 55 hours. 0.5 ml samples of the liquefaction/saccharification reaction were withdrawn at different time intervals, combined with 4.5 ml of RO water and boiled for 10 minutes. Samples were cooled down and then filtered using a 0.2 μm disc filter (Titan Syringe Filter PTFE) prior to HPLC analysis. The HPLC analysis was conducted using a Phenomenex RHM column. The composition of the various sugars and the starch solubilization in the liquefaction/saccharification mixtures is presented in Table 3.

TABLE 3

Composition of sugars and starch solubilization during simultaneous liquefaction/saccharification of granular starch at 28% DS using HgGA.

| % dry solids | HgGA dose, GAU/g ds | Time (Hours) | % starch solubility | % of Sugars, 60° C., pH 5.5 | | | |
|---|---|---|---|---|---|---|---|
| | | | | % DP1 | % DP2 | % DP3 | % HS |
| 28% | 0.2 | 6.25 | 67.94 ± 0.06 | 96.97 ± 0.03 | 2.41 | 0.63 | 0 |
| | 0.25 | 6.25 | 70.83 ± 0.03 | 95.37 ± 0.14 | 2.15 | 0.67 | 1.81 |
| | 0.3 | 6.25 | 73.71 ± 1.16 | 95.03 ± 0.04 | 1.87 | 0.76 | 2.34 |
| 28% | 0.2 | 22 | 89.53 ± 0.14 | 95.75 ± 0.01 | 2.01 | 1.31 | 0.93 |
| | 0.25 | 22 | 91.44 ± 0.14 | 95.45 ± 0.27 | 1.79 | 1.19 | 1.56 |
| | 0.3 | 22 | 93.13 ± 0.75 | 94.77 ± 0.20 | 1.66 | 1.04 | 2.53 |
| 28% | 0.2 | 28 | 92.85 ± 0.24 | 96.32 ± 0.38 | 1.68 | 0.99 | 1.00 |
| | 0.25 | 28 | 94.28 ± 0.17 | 95.67 ± 0.30 | 1.58 | 1.05 | 1.69 |
| | 0.3 | 28 | 95.54 ± 0.54 | 94.47 ± 0.52 | 1.62 | 1.21 | 2.70 |
| 28% | 0.2 | 50 | 97.58 ± 0.28 | 96.30± | 2.54 | 0.37 | 0.80 |
| | 0.25 | 50 | 97.73 ± 0.11 | 96.42 ± 0.29 | 2.79 | 0.30 | 0.49 |
| | 0.3 | 50 | 97.54 ± 0.74 | 96.30 ± 0.45 | 3.10 | 0.31 | 0.28 |

As shown in Table 3, simultaneous liquefaction/saccharification of granular corn starch at a single pH resulted in a 95%+ glucose syrup (DP1) with 90+% starch solubility after 28 hrs of incubation for all of the HgGA dosages tested. After 50 hours the glucose syrup (DP1) content increased to 96+% with a starch solubility of 97%, higher sugar (HS) content is below 1% for all of the HgGA dosages. The data in Table 3 indicate that a simultaneous liquefaction/saccharification can effectively be achieved in a single pH and temperature process with HgGA in combination with an alpha-amylase.

What is claimed is:

1. A method of processing a starch comprising saccharification of a starch substrate to glucose in the presence of a glucoamylase without a pH adjustment, wherein saccharification is performed at pH 5.2 to 5.6 and at a temperature in the range of about 58° C. to about 62° C., wherein the glucoamylase is selected from the group consisting of a parent *Humicola grisea* glucoamylase (HgGA) comprising SEQ ID NO: 3 and a variant thereof, wherein the variant has at least 99% identity to the parent glucoamylase.

2. The method of claim 1, wherein saccharification is performed in the presence of a pullulanase.

3. The method of claim 1, wherein the variant glucoamylase has at least one amino acid modification compared to the parent glucoamylase.

4. The method of claim 1, wherein the glucoamylase is HgGA having amino acid sequence of SEQ ID NO: 3.

5. The method of claim 1, wherein the glucoamylase is produced in a *Trichoderma reesei* host cell.

6. The method of claim 1, wherein the glucoamylase is added at a dose of at least about 0.15 GAU per gram of dry substance starch.

7. The method of claim 1, wherein the glucoamylase is added at a dose of at least about 0.20 GAU per gram of dry substance starch.

8. The method of claim 1, wherein saccharification is carried out at pH 5.35 to 5.5.

9. The method of claim 1, wherein the starch substrate is liquefied starch.

10. The method of claim 1, wherein saccharification achieves a DP1 concentration of at least 95% at about 70 hours.

11. The method of claim 1, wherein the starch substrate is about 30% to about 50% dry solids (DS).

12. The method of claim 11, wherein the starch substrate is about 30% to about 35% dry solids (DS).

13. The method of claim 1, wherein the starch substrate is granular starch.

14. The method of claim 13, wherein saccharification achieves a DP1 concentration of at least 95% at about 28 hours.

15. The method of claim 14, wherein the starch solubility of the starch substrate is at least 90%.

16. The method of claim 13, wherein saccharification achieves a DP1 concentration of at least 96% at about 50 hours.

17. The method of claim 16, wherein the starch solubility of the starch substrate is at least 97%.

18. The method of claim 16, wherein the higher sugar content is below 1%.

19. The method of claim 13, wherein the starch substrate is about 28% dry solids (DS).

\* \* \* \* \*